US008634919B1

(12) United States Patent
Hou et al.

(10) Patent No.: US 8,634,919 B1
(45) Date of Patent: Jan. 21, 2014

(54) INTRACARDIAC IMPLANTABLE MEDICAL DEVICE FOR BIATRIAL AND/OR LEFT HEART PACING AND METHOD OF IMPLANTING SAME

(71) Applicant: Pacesetter, Inc., Sylmar, CA (US)

(72) Inventors: Wenbo Hou, Valencia, CA (US); Xiaoyi Min, Camarillo, CA (US); Edward Karst, South Pasadena, CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 13/722,878

(22) Filed: Dec. 20, 2012

(51) Int. Cl.
*A61N 1/375* (2006.01)
(52) U.S. Cl.
USPC .............................. 607/36; 607/122
(58) Field of Classification Search
USPC ..................................... 607/36, 122
See application file for complete search history.

(56) References Cited

U.S. PATENT DOCUMENTS

| 6,200,265 | B1 | 3/2001 | Walsh et al. |
| 6,585,707 | B2 | 7/2003 | Cabiri et al. |
| 7,310,556 | B2 * | 12/2007 | Bulkes ............................ 607/33 |
| 7,894,915 | B1 | 2/2011 | Chitre et al. |
| 2002/0028991 | A1 | 3/2002 | Thompson |
| 2012/0158074 | A1 | 6/2012 | Hall |
| 2013/0023975 | A1 * | 1/2013 | Locsin .......................... 607/122 |

FOREIGN PATENT DOCUMENTS

| EP | 1171201 B1 | 8/2004 |
| WO | 2009147678 A2 | 12/2009 |

* cited by examiner

*Primary Examiner* — Michael Kahelin

(57) ABSTRACT

An intra-cardiac implantable medical device (IIMD) and method of implant are provided. The IIMD comprises a housing configured to be implanted entirely within a coronary sinus (CS) of the heart. The IIMD has at least one intra-cardiac device extension (ICDE).

9 Claims, 12 Drawing Sheets

US 8,634,919 B1

INTRACARDIAC IMPLANTABLE MEDICAL DEVICE FOR BIATRIAL AND/OR LEFT HEART PACING AND METHOD OF IMPLANTING SAME

BACKGROUND OF THE INVENTION

Embodiments of the present invention generally relate to intra-cardiac implantable devices and methods for implanting the same. Embodiments more particularly relate to intra-cardiac implantable medical devices that utilize an IC device extension to afford dual chamber functionality.

Currently, permanently-implanted pacemakers (PPMs) utilize one or more electrically-conductive leads (which traverse blood vessels and heart chambers) in order to connect a canister with electronics and a power source (the can) to electrodes affixed to the heart for the purpose of electrically exciting cardiac tissue (pacing) and measuring myocardial electrical activity (sensing). These leads may experience certain limitations, such as incidences of venous stenosis or thrombosis, device-related endocarditis, lead perforation of the tricuspid valve and concomitant tricuspid stenosis; and lacerations of the right atrium, superior vena cava, and innominate vein or pulmonary embolization of electrode fragments during lead extraction. Further, conventional pacemakers with left ventricle (LV) pacing/sensing capability require multiple leads and a complex header on the pacemaker.

A small sized PPM device has been proposed with leads permanently projecting through the tricuspid valve and that mitigate the aforementioned complications. This PPM is a reduced-size device, termed a leadless pacemaker (LLPM) that is characterized by the following features: electrodes are affixed directly to the "can" of the device; the entire device is attached to the heart; and the LLPM is capable of pacing and sensing in the chamber of the heart where it is implanted.

LLPM devices, that have been proposed thus far, offer limited functional capability. These LLPM devices are able to sense in one chamber and deliver pacing pulses in that same chamber, and thus offer single chamber functionality. For example, an LLPM device that is located in the right atrium would be limited to offering AAI mode functionality. An AAI mode LLPM can only sense in the right atrium, pace in the right atrium and inhibit pacing function when an intrinsic event is detected in the right atrium within a preset time limit. Similarly, an LLPM device that is located in the right ventricle would be limited to offering WI mode functionality. A WI mode LLPM can only sense in the right ventricle, pace in the right ventricle and inhibit pacing function when an intrinsic event is detected in the right ventricle within a preset time limit.

It has been proposed to implant sets of multiple LLPM devices within a single patient, such as one or more LLPM devices located in the right atrium and one or more LLPM devices located in the right ventricle. The atrial LLPM devices and the ventricular LLPM devices wirelessly communication with one another to convey pacing and sensing information there between to coordinate pacing and sensing operations between the various LLPM devices.

However, these sets of multiple LLPM devices experience various limitations. For example, each of the LLPM devices must expend significant power to maintain the wireless communications links. The wireless communications links should be maintained continuously in order to constantly convey pacing and sensing information between, for example, atrial LLPM device(s) and ventricular LLPM device(s). This pacing and sensing information is necessary to maintain continuous synchronous operation, which in turn draws a large amount of battery power. Also, it is difficult to maintain a reliable wireless communications link between LLPM devices. Moreover, LLPM systems have not yet sufficiently addressed suppression of atrial fibrillation (AF), nor afforded bi-atrial pacing/sensing capabilities.

SUMMARY

In accordance with one embodiment, an intra-cardiac implantable medical device (IIMD) is comprised of a housing configured to be implanted entirely within a coronary sinus (CS) of the heart. The housing includes opposed proximal and distal ends configured to be positioned at a first implant location within the CS such that the proximal end is directed toward an ostium (OS), and the distal end is directed toward vessels branching from the CS. A first intra-cardiac device extension (ICDE) has a first extension body that is electrically and physically attached to the proximal end of the housing. The first extension body including a first transition segment and a first active segment, the first transition segment extending along the CS toward the OS. A first electrode is provided on the first active segment and configured to be positioned at a first activation site proximate to a first chamber of interest when the first extension body is in a fully deployed state. A second ICDE has a second extension body that is electrically and physically attached to the distal end of the housing, the second extension body including a second transition segment and a second active segment. The second transition segment extends along the CS away from the OS toward a vessel of interest. A second electrode is provided on the second active segment and configured to be positioned at a second activation site proximate to a second chamber of interest when the second extension body is in a fully deployed state and a controller, within the housing, configured to cause stimulus pulses to be delivered, in synchronous manner, through the first and second electrodes to the first and second activation sites, respectively.

The first and second transition segments are sufficient in length to locate the first and second active segments distal from the housing of the IIMD such that the first and second electrodes are located in at least one of a right atrium, the CS and a vein of Marshall branching from the CS.

The first transition segment is sufficient in length to extend back through the OS to locate the first active segment distal from the housing of the IIMD with the first electrode located at the first activation site in a right atrium.

Optionally, the second transition segment may be sufficient in length to extend into the vein of Marshall to locate the second active segment distal from the housing of the IIMD with the second electrode located in the vein of Marshall and proximate to the second activation site in a left atrium. Optionally, the IIMD further comprises a third electrode provided on the housing, the third electrode configured to be located proximate to a third implant side, the third implant side associated with one of the right atrium and left atrium.

The first extension body may be formed of a flexible biocompatible material having a pre-formed curved shape with at least first and second bends that project in opposed transverse directions, relative to a longitudinal axis of the housing, to engage the vessel of interest when in the deployed state. The second extension body may be formed of a flexible biocompatible material having a pre-formed L-shape with an elbow portion provided between proximal and distal leg portions, the elbow directing the distal leg into the vein of Marshall. The first and second extension bodies may be formed of materials having shape memory characteristics that allow the first and second extension bodies to transform between a collapsed state and an expanded deployed state. The controller may be configured to identify atrial fibrillation and cause delivery of an atrial antitachycardia pacing (AATP) therapy.

In accordance with an embodiment, a method is provided of implanting an intra-cardiac system that comprises an intra-cardiac implantable medical device and first and second intra-cardiac device extensions joined to distal and proximal ends of the IIMD, respectively. The method comprises maneuvering an introducer assembly through a local chamber of a heart toward a coronary sinus, positioning the first ICDE at a first implant location such that a first electrode on the first ICDE is located at a first activation site in a vessel of interest proximate to a first chamber, and positioning the second ICDE at a second implant location such that a second electrode on the second ICDE is located at a second activation site proximate to a second chamber. The method maintains at least one of the first and second ICDEs in an elongated collapsed state while maneuvering the first and second ICDEs to the first and second implant locations, respectively, and permits the at least one of the first and second ICDEs to deploy to a preformed shape that extends in a transverse direction relative to a longitudinal axis of the IIMD in order to abut against a wall of the vessel of interest.

The ICDE positioning operation may further comprises advancing a placement tool within the sheath to engage the first ICDE, the placement tool maintaining the first ICDE in the elongated collapsed state while maneuvering the first ICDE to the first implant location and disengaging the placement tool from the first ICDE once the first ICDE is at the first implant location, the first ICDE returning to the preformed shape when the placement tool is disengaged. The first ICDE positioning operation may include positioning the first ICDE in the vein of Marshall such that the first electrode is located proximate to a left atrium. The second ICDE positioning operation may include positioning the second ICDE in the coronary sinus such that the second activation site is in the coronary sinus proximate to a right atrium that represents the second chamber. The second ICDE positioning operation may include positioning the second ICDE to extend from the coronary sinus through the ostrium into the right atrium such that the second activation site is in a right atrium that represents the second chamber.

Optionally, the first ICDE may return to an L-shape representing a first preformed shape and the second ICDE may return to an S-shape representing a second preformed shape.

The introducer assembly includes a sheath in which the IIMD and first and second ICDEs are loaded. The method may comprise maneuvering the sheath into the coronary sinus and discharging the IIMD and the first and second ICDEs from the distal end of the sheath into the coronary sinus. The method may further comprise configuring a controller, within the IIMD, to cause stimulus pulses to be delivered, in a dual chamber synchronous manner, through the first and second electrodes to the first and second activation sites, respectively. The method may further comprise inserting a pusher rod into the sheath, removably connecting the pusher rod to the IIMD, and utilizing the pusher rod to push the IIMD out of the sheath. The method may further comprise inserting a placement tool into the sheath, engaging at least one of the first and second ICDEs with the placement tool, and utilizing the placement tool to maneuver at least one of the first and second ICDEs to the first and second activation sites, respectively. The method may further comprise attaching a placement tool to at least one of the first and second ICDEs, and manipulating the placement tool to position the at least one of the first and second ICDEs at the first and second implant locations. The method may further comprise attaching a pusher tool to the IIMD, and manipulating the pusher tool to position the IIMD at the second implant location.

Optionally, when the IIMD and the first and second ICDEs are loaded into the lumen, the lumen may have an inner diameter that maintains the first and second ICDEs in the elongated collapsed state, the first and second ICDEs returning to the preformed shape when in the deployed state after being discharged from a distal end of the sheath.

In accordance with an embodiment, an intra-cardiac implantable medical device (IIMD), is provided that comprises a housing configured to be implanted entirely within the CS of the heart. The housing includes opposed proximal and distal ends, configured to be positioned at a first implant location within the CS such that the proximal end is directed toward the OS and the distal end is directed toward vessels branching from the CS. A first intra-cardiac device extension has a first extension body that is electrically and physically attached to the distal end of the housing. The first extension body includes a first transition segment and a first active segment. The first transition segment extends along the CS away from the OS, the first activation segment extending into a vein of Marshall representing a vessel of interest. A first electrode is provided on the first active segment and configured to be positioned at a first activation site in the vein of Marshall proximate to a left atrium when the first extension body is in a fully deployed state. A second electrode is provided on the housing and configured to be positioned at a second activation site proximate to a second chamber of interest. A controller, within the housing, is configured to cause stimulus pulses to be delivered, in a synchronous manner, through the first and second electrodes to the first and second activation sites, respectively.

In accordance with an embodiment, a method is provided for implanting an intra-cardiac system that comprises an intra-cardiac implantable medical device (IIMD) and an intra-cardiac device extension (ICDE) joined to a distal end of the IIMD. The method comprises maneuvering an introducer assembly through a local chamber of a heart toward a coronary sinus, and positioning the ICDE at a first implant location such that a first electrode on the ICDE is located at a first activation site in the vein of Marshall which represents a vessel of interest, the first activation site being proximate to a left atrium which represents a first chamber. The method maneuvers the IIMD to position a second electrode, on a housing of the IIMD, at a second implant location such that the second electrode is located at a second activation site proximate to a second chamber. The method maintains the ICDE in an elongated collapsed state while maneuvering the first ICDE to the first implant location and permits the ICDE to deploy to an preformed shape that extends in a transverse direction relative to a longitudinal axis of the IIMD in order to project into the vein of Marshall.

Optionally, the method further comprises of attaching a placement tool to the ICDE, and manipulating the placement tool to position the ICDE at the first implant location. Optionally, the method further comprises attaching a pusher tool to the IIMD, and manipulating the pusher tool to position the IIMD at the second implant location. Optionally, the method further comprises utilizing a stylet or guide wire as a placement tool to maintain the ICDE in the elongated collapsed state.

DETAILED DESCRIPTION

Figure 1A:
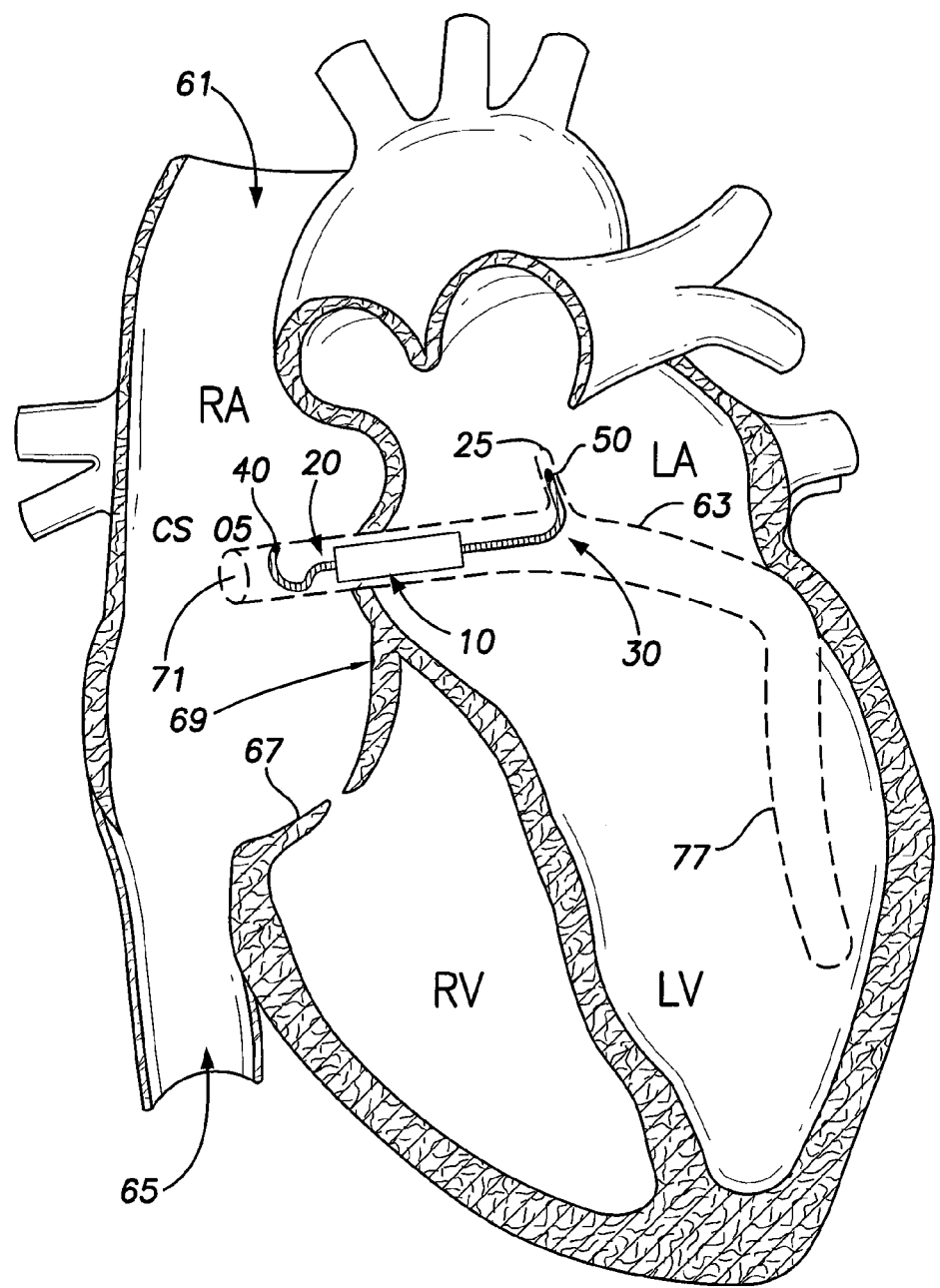
FIG. 1A illustrates a side view of the chambers of the heart including the right atrium, left atrium, right ventricle and left ventricle with an IIMD implanted in accordance with an embodiment.

FIG. 1A illustrates a side view of the chambers of the heart including the right atrium (RA), left atrium (LA), right ventricle (RV) and left ventricle (LV). FIG. 1A further illustrates the coronary sinus (CS) and the ostium (OS) of the CS. An intracardiac implantable medical device (IIMD) 10 is illustrated to be implanted within the coronary sinus. The IIMD 10 may have been placed through the superior vena cava (SVC) or inferior vena cava (IVC) into the right atrium of the heart. As shown in FIG. 1A, the right atrium wall includes the superior vena cava inlet 61, coronary sinus 63, IVC inlet 65, tricuspid valve 67, and the ventricular vestibule (VV) region 69. The ostium 71 represents the juncture of the coronary sinus 63 and the RA. The coronary sinus branches into various tributary vessels such as the lateral veins, great cardiac vein, middle cardiac vein, small cardiac vein, anterior interventricular veins and the like. In FIG. 1A, the lateral cardiac vein 77 and vein of Marshall 25 are denoted with reference numbers as examples. The lateral cardiac vein 77 extends along the LV toward the LV apex. The vein of Marshall 25 extends along a side of the LA.

The IIMD 10 includes intracardiac device extensions (ICDE) 20 and 30 electrically and mechanically coupled to opposed ends of the IIMD 10 and extending in opposite directions therefrom. The ICDEs 20 and 30 have one or more electrodes provided thereon. In the example of FIG. 1A, tip electrodes 40 and 50 are shown provided on the distal ends of the ICDEs 20 and 30, respectively. Optionally, all or a portion of the housing of the IIMD 10 may be formed as one or more additional electrodes. As one example, the tip electrodes 40 and 50 may be configured to represent anode electrodes, while all or a portion of the housing of the IIMD 10 may be configured to operate as a cathode electrode. The ICDE 30 has an outer portion that is deflected and extends into a vessel branching from the coronary sinus, namely the vein of Marshall 25, thereby locating the electrode 50 proximate to the LA.

In accordance with embodiments herein, the IIMD 10 and ICDEs 20 and 30 are small enough to be delivered into the coronary sinus through the OS without interfering with normal blood flow in the CS. One or more electrodes may be attached to opposite ends of the ICDEs 20 and 30 and electrically connected to the control system within the IIMD 10 via flexible extension bodies made of biocompatible materials, such as polymers and the like. The extension bodies of the ICDEs 20 and 30 separate electrodes at suitable distances based upon desired activation sites and chambers of interest. As one example, one ICDE 30 may locate an electrode 50 proximate to the left atrium to form an LA electrode. The LA electrode is provided on an extension body that is preshaped to bend up or transversely (relative to the longitudinal axis of the IIMD) in order to be able to be securely positioned or wedged into the vein of Marshall or another vessel of interest. An opposed ICDE 20 has one or more electrodes 40 thereon that are configured to be located proximate to or within the RA, thereby forming an RA electrode. The RA electrode is provided on an extension body that may be preshaped into an S-shape or other similar shape such that, after an introducer assembly is removed, the extension body will return to its original shape in which the RA electrode engages tissue of interest in or proximate to the RA in order to pace and sense the RA. The RA and LA electrodes are configured to be able to sense and pace the RA and LA in a simultaneous or coordinated manner from within the coronary sinus (and vein of Marshall) as shown in FIG. 1A.

In one embodiment, the housing of the IIMD 10 may be formed as a flexible leadless pacer body for which the dimensions of the leadless pacer are designed to fit in the CS anatomy. As one example, the IIMD 10 may be formed with a long and thin tubular housing with multiple sections, each of which includes various portions of the IIMD functionality, such as the electronics, battery, storage capacitors and the like. Flexible connectors may be utilized to interconnect the separate segments of the long thin tubular body. Optionally, the overall housing of the IIMD 10 may be formed as one body. In various embodiments, the IIMD 10 may be formed with a rigid metallic body in ring structure that contains a battery, capacitors and electronics. Flexible biocompatible polymer body extensions are connected to opposite ends of the IIMD 10 housing and have the RA and LA electrodes provided on distal ends thereof.

The controller of the IIMD 10 may be configured to provide bi-atrial pacing and sensing. The IIMD 10 may perform bi-polar pacing of the RA and LA with pacing and/or sensing vectors formed between the RA electrode to the IIMD housing, between the LA electrode and the IIMD housing, and/or between the RA and LA electrodes. The system may be configured to perform dual chambered pacing and sensing (e.g. in a DDD mode). As explained hereafter, embodiments herein provide an IIMD 10 that may utilize passive fixation mechanisms to maintain the device in place. For example, the flexible ICDE may be designed to bend toward the LA and to be placed into the vein of Marshall to afford passive fixation. The IIMD 10 may be configured to sense in the LA and RA, identify AF and in response thereto deliver atrial antitachycardia pacing (ATTP) therapy. For example, by pacing the LA through the vein of Marshall, the system may afford suppression of AF given that the LA electrode is located close to the AF origin.

Figure 1B:
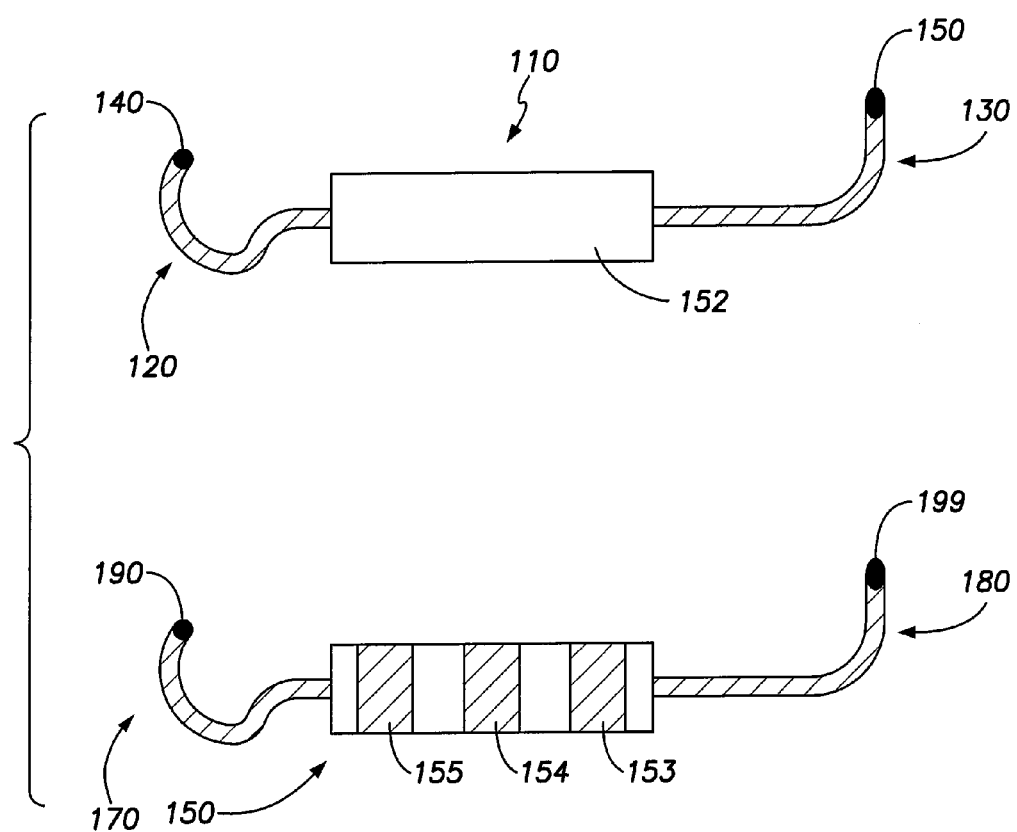
FIG. 1B illustrates two alternative IIMD configurations implemented in accordance with embodiments herein.

FIG. 1B illustrates two alternative IIMD configurations implemented in accordance with embodiments herein. A first IIMD 110 has first and second ICDEs 120 and 130 extending from opposite ends thereof. The first and second ICDEs 120 and 130 have tip electrodes 140 and 150, respectively, on distal ends of the ICDEs 120 and 130. The housing of the IIMD 110 forms one complete electrode 152.

An alternative configuration within FIG. 1B illustrates an IIMD 150 having ICDEs 170 and 180 provided on opposite ends thereof. Tip electrodes 190 and 199 are located on distal ends of the ICDEs 170 and 180. The housing of the IIMD 150 includes multiple separate electrodes 153-155. The electrodes 153-155 may be electrically common in connection with pacing and sensing. Alternatively, the electrodes 153-155 may be electrically separated from one another for one or both of pacing and sensing. As one example, all of the electrodes 153-155 may be used as a common electrode in connection with pacing or sensing, but yet only one or a subset of electrodes 153-155 may be used during sensing or pacing.

Figure 2A:
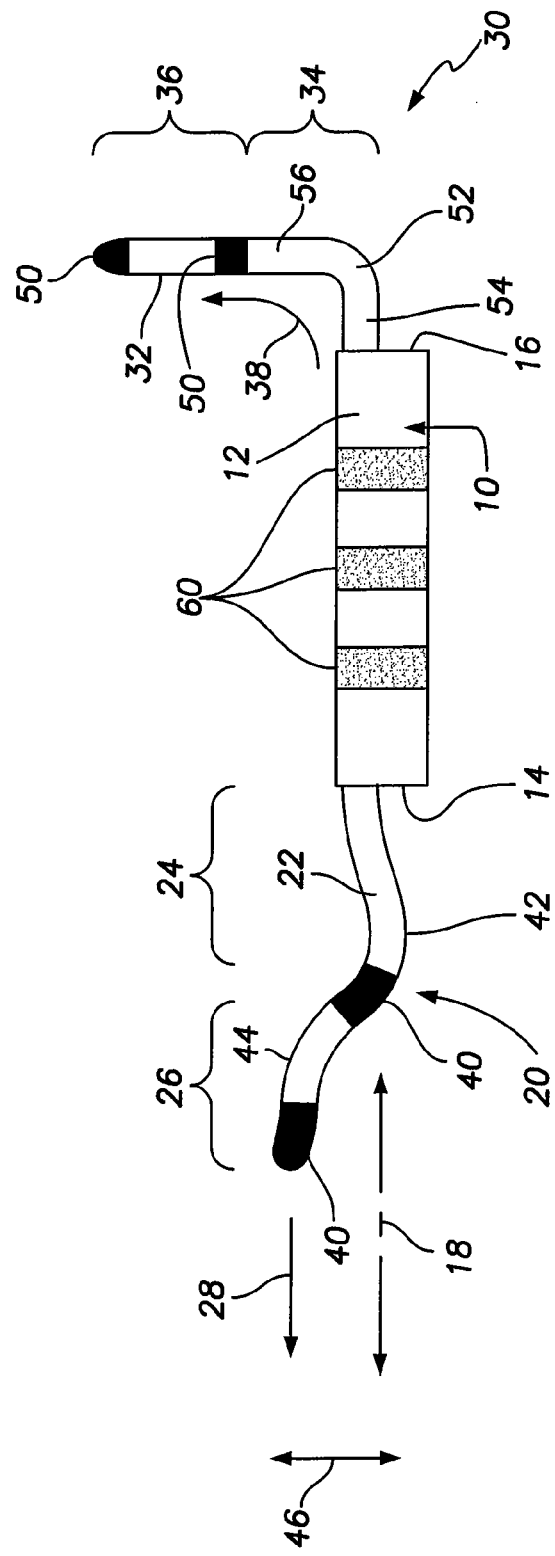
FIG. 2A illustrates that intracardiac implantable medical device of FIG. 1A in more detail formed in accordance with an embodiment, when in a deployed position and state.

FIG. 2A illustrates the IIMD 10 of FIG. 1A in more detail formed in accordance with an embodiment, when in a deployed position and state. The IIMD 10 includes a housing 12 having a proximal end 14 and a distal end 16. The housing 12 is long and tubular, and extends along a longitudinal axis 18 between the proximal and distal ends 14, 16. A first ICDE 20 is electrically and physically attached to the proximal end 14 of the housing 12. The ICDE 20 includes an extension body 22 formed of a biocompatible material that has first transition and active segments 24 and 26. The first transition segment 24 extends along the CS towards the OS. At least one electrode 40 is provided on the active segment 26. The electrodes 40 are configured to be positioned at a first activation site that is proximate to a first chamber of interest when the extension body 24 is in a fully deployed state.

The extension body 22 may be a preformed in a curved shape. For example, the curved shape may include one or more bends 42 and 44 that project in generally opposite transverse directions 46 relative to the longitudinal axis 18 of the housing 12. The bends 42 and 44 project outward in opposed transverse directions until engaging the wall of the vessel of interest. The electrodes 40 are located on the extension body 22 at positions relative to the bends 42 and 44 such that, when the ICDE 20 is in the fully deployed state, the electrodes 40 securely press against the wall of the vessel of interest at the desired first activation site.

A second ICDE 30 is electrically and physically attached to the distal end 16 of the housing 12. The second ICDE 30 includes an extension body 32 that projects outward from the distal end 16 of the housing 12. The second extension body 32 includes a second transition segment 34 and a second activation segment 36. The transition segment 34 extends along the CS away from the OS toward and into a vessel of interest as generally denoted by the extension direction 38.

One or more electrodes 50 are provided on the activation segment 36 and are configured to be positioned at a second activation site proximate to a second chamber of interest when the extension body 32 is in the fully deployed state. As one example, the extension body 32 may be formed from a flexible biocompatible material having a preformed L shape. For example the L shape may include an elbow portion 52 that is formed integral with proximal and distal legs 54 and 56. The elbow 52 is configured to direct the distal leg 56 into a vessel of interest, such as into the vein of Marshall. The proximal leg 54 has a length sufficient to position the housing 12 of the IIMD 10 at a desired location with the CS relative to the intersection of the vein of Marshall and the CS.

The ICDEs 20 and 30 may be permanently or removably coupled to the proximal and distal ends 14 and 16.

Optionally, the IIMD 10 may include one or more electrodes 60 provided about the housing 12. The electrode 60 may be positioned on the housing 12 and configured to be located proximate to a third implant site. As one example, the third implant site may be associated with an atrial-ventricular (AV) node, or one of the right and left atrium.

As one example, the first and second transition segments 24 and 34 may have lengths sufficient to locate the first and second active segments 26 and 36 distal from the housing 12 such that the first and second electrodes 40 and 50 are located in at least one of the right atrium, the CS and the vein of Marshall branching from the CS. For example, the electrodes 40 may be positioned within the CS near the OS as a first activation site, in order to stimulate the right atrium. As another example, the transition segment 24 may be longer such that the entire active segment 26 extends out of the OS back into the right atrium with the bends 42 and 44 curling the active segment 26 in order that one or more of electrodes 40 directly engage the wall in the right atrium.

Optionally, one or more active fixation members (e.g., helix, fish hook, spike, retractable hook) may be provided on a distal end of the active segment 32 and/or on the distal end of the active segment 26 at, near, or as part of electrodes 50 and/or 40.

The ICDE 30 may be dimensioned such that the active segment 36 extends into the veining of Marshall with the electrodes 50 touching the wall of the vein of Marshall as the second activation site proximate to the left atrium. The electrodes 40 and 50 are located distal from the housing 12 in order to be located at activation sites of interest proximate to the left and right atrium.

Figure 2B:
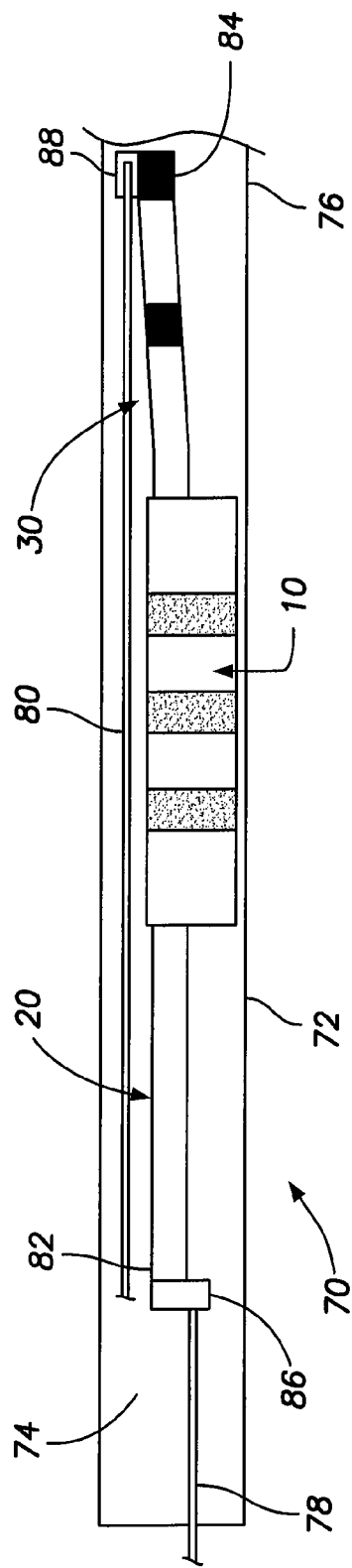
FIG. 2B illustrates the IIMD of FIG. 1A during an implantation process when loaded into an introducer assembly in accordance with an embodiment.

FIG. 2B illustrates the IIMD 10 during an implantation process when loaded into an introducer assembly 70 having a sheath 72. The sheath 72 has a lumen 74 dimensioned to receive the IIMD 10, as well as the ICDEs 20 and 30. A distal end 76 of the sheath 72 is open to permit deployment at desired activation sites. In the example of FIG. 2B, placement tools 78 and 80 are illustrated to be coupled to ICDE distal ends 82 and 84. As one example, connectors 86 and 88 may be provided on the placement tools 78 and 80 and/or on the distal ends 82 and 84 of the ICDEs 20 and 30. As one example, the placement tools 78 and 80 may represent stylets having outer ends that fit into receptacles within the connectors 86 and 88. The outer ends of the stylets (as placement tools 78 and 80) may be retained in the connectors 86 and 88 until the ICDEs 20 and 30 are in desired implant locations.

Initially, during deployment, the sheath 72 is held over the IIMD 10 and ICDEs 20 and 30 to maintain the ICDEs 20 and 30 in a generally linear or straight, gradually bending configuration, that follows the sheath 72, while the sheath 72 is maneuvered into a desired chamber of the heart and then into the CS through the ostium. Once the sheath 72 is maneuvered a desired distance into the CS, a first deployment stage may be initiated. As one example, this initial deployment stage may involve manipulating and locating the ICDE 30 into a vessel of interest from the CS, such as the vein of Marshall.

Figure 2C:
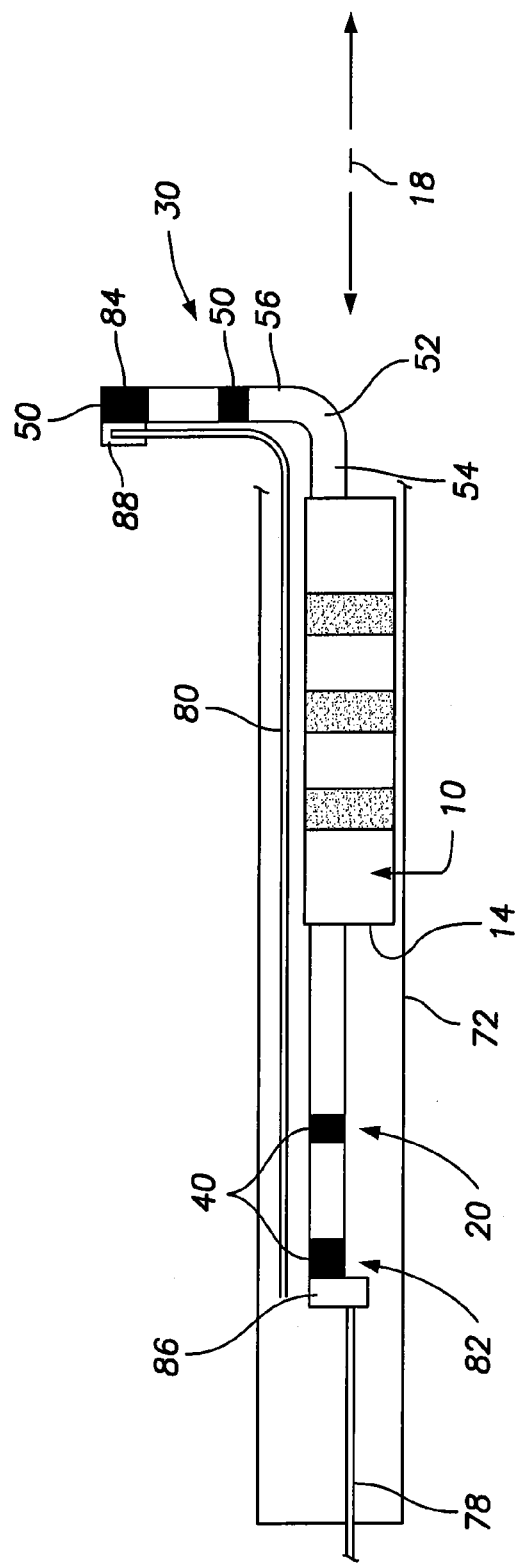
FIG. 2C illustrates the IIMD of FIG. 1A with the ICDE in an initial deployed position in accordance with an embodiment.

FIG. 2C illustrates the IIMD 10 with the ICDE 30 in an initial deployed position. In FIG. 2C, the sheath 72 has been partially withdrawn by a distance sufficient to expose the ICDE 30 from the distal end 76. As the sheath 72 is withdrawn, the ICDE 30 is permitted to return to its preformed initial shape, in which the bend 52 orients the leg 56 at a desired acute or obtuse angle extending transverse to the longitudinal axis 18 of the IIMD 10. As the ICDE 30 is deployed from the sheath 72, the placement tool 80 remains coupled to the ICDE distal end 84 at the connector 88. The placement tool 80 may be used to manipulate the distal end 84 of the ICDE 30 until the electrodes 50 are located proximate and engaged tissue wall for the vessel of interest at a desired activation site proximate to the LA. Once the electrode 50 is located in the desired positions, the placement tool 80 may be removed by disconnecting the outer end of the placement tool 80 from the distal end 84. As part of the disconnection operation, the connector 88 may remain coupled to the distal end 84 or alternatively may be removed from the distal end 84 and withdrawn with the placement tool 80. Throughout the deployment stage associated with the ICDE 30, the proximal ICDE 20 is held within the sheath 72 and connected to the placement tool 78.

Next, the implantation process moves to a second ICDE implant stage at which the ICDE 20 is positioned and maneuvered to a desired activation site proximate to a chamber of interest, such as the right atrium. To position the ICDE 20, the sheath 72 is entirely removed to expose the ICDE 20, but while maintaining a connection between the placement tool 78 and the distal end 82 at connector 86. Placement tool 78 is then used to position the distal end 82 in a desired position as the extension body 22 returns to its preformed shape, such as the shape illustrated in FIG. 2A. Once the placement tool 78 has positioned the electrodes 40 in the desired activation site, the placement tool 78 is disconnected from the distal end 82. As explained above, the connector 86 may remain on the distal end 82 or may be removed with the placement tool 78.

Optionally, the placement tool 78 may be entirely removed and the ICDE 20 permitted to deploy to its activation site simply while the sheath 72 is being removed. As a further option, an additional placement tool, such as a pusher (not shown) may be connected to the IIMD 10 at the proximal end 14 to hold the IIMD 10 in a desired position while the sheath 72 is withdrawn. In this alternative exemplary configuration, when a pusher tool is connected to the IIMD 10, the placement tool 78 may not be needed and thus may be entirely omitted. As a further option, when a placement tool such as a pusher is connected to the IIMD 10, the placement tool 80 may also be entirely omitted and the ICDE 30 permitted to advance to its desired position simply through adjustment and shifting of the sheath 72 and IIMD 10 under the control of a pusher.

Figure 3A:
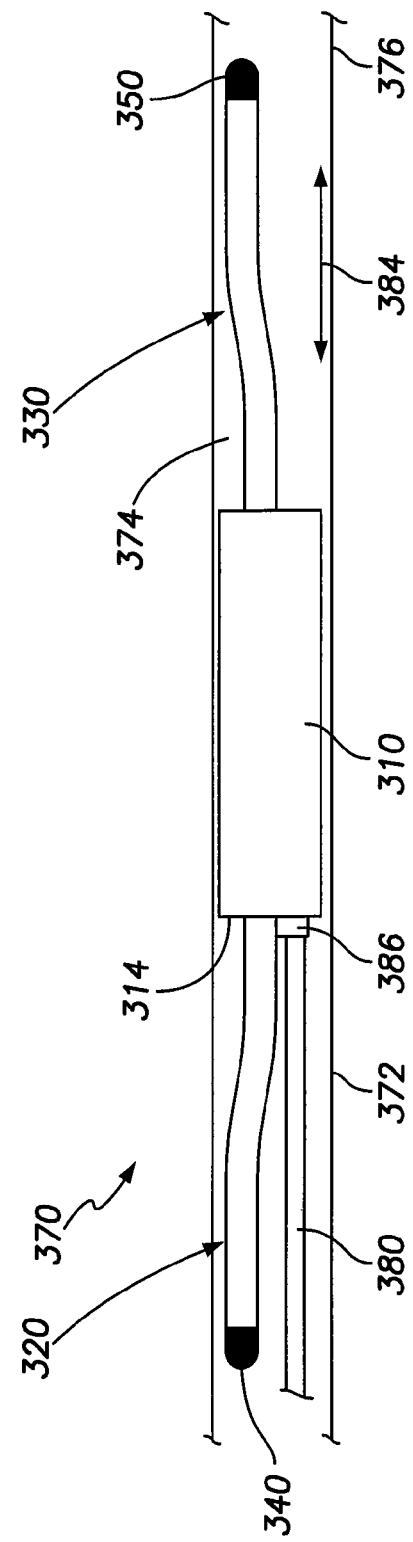
FIG. 3A illustrates an IIMD and ICDEs in accordance with an embodiment, when utilized in connection with an alternative introducer assembly.

FIG. 3A illustrates an IIMD 310 and ICDEs 320 and 330 formed in accordance with an alternative embodiment, when utilized in connection with an alternative introducer 370. The introducer 370 includes a sheath 372 with an open distal end 376. A pusher tool 380 is coupled at a connector 382 to the proximal end 314 of the IIMD 310. In the example of FIG. 3A, there are no placement tools directly coupled to the ICDEs 320 and 330. The pusher tool 380 may be used to shift the IIMD 310 and ICDEs 320 and 330 in a longitudinal direction 384 relative to the sheath 372 in order to deploy and retract the ICDEs 320 and 330 and IIMD 310 from the distal end 376. As explained above, the sheath 372 is used to advance and manipulate the overall assembly through the right atrium through the OS to the CS.

The sheath 372 includes a lumen 374 into which the IIMD 310 and ICDEs 320 and 330 are loaded. The lumen 374 has an inner diameter dimensioned to maintain the ICDEs 320 and 330 in the elongated generally collapsed state until deployed. The ICDEs 320 and 330 return to the deployed state after discharged from the distal end 376 of the sheath 372.

Figure 3B:
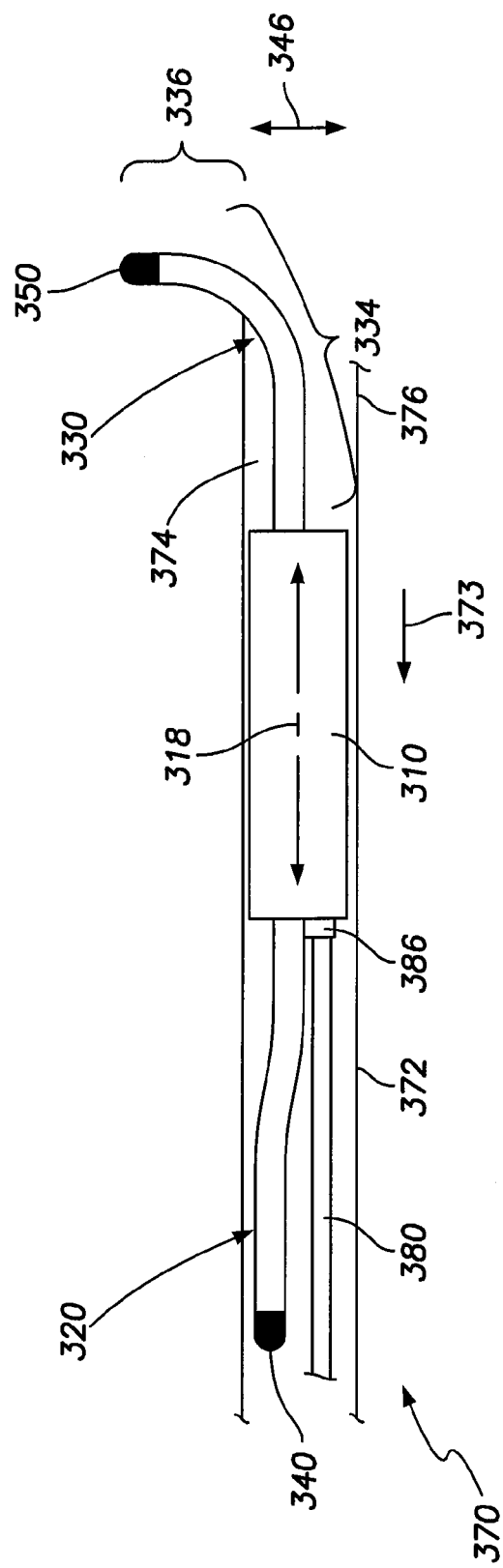
FIG. 3B illustrates the IIMD of FIG. 3A when at a partially deployed stage from the introducer assembly.

FIG. 3B illustrates the IIMD 310 when at a partially deployed stage from the introducer assembly 370. When partially deployed, the sheath 372 is partially retracted in the direction of arrow 373 to expose the active segment 336 on the ICDE 330. As the active segment 336 is exposed beyond the distal end 376, the preformed shape of the ICDE 330 causes the active segment 336 to laterally deflect in the direction of arrow 346. When laterally deflected in the transverse direction 346, the electrode 350 is directed in a direction extending at and up to, perpendicular or acute angle with respect to the longitudinal axis 318 of the housing of the IIMD 310. The pusher 380 and sheath 372 are manipulated in cooperation with one another to maneuver the active segment 336 into a vessel of interest branching from the coronary sinus, such as into the vein of Marshall. This cooperative motion between the pusher 380 and sheath 372 continues as a great portion of the ICDE 330 is deployed from the distal end 376 of the sheath 372.

Figure 3C:
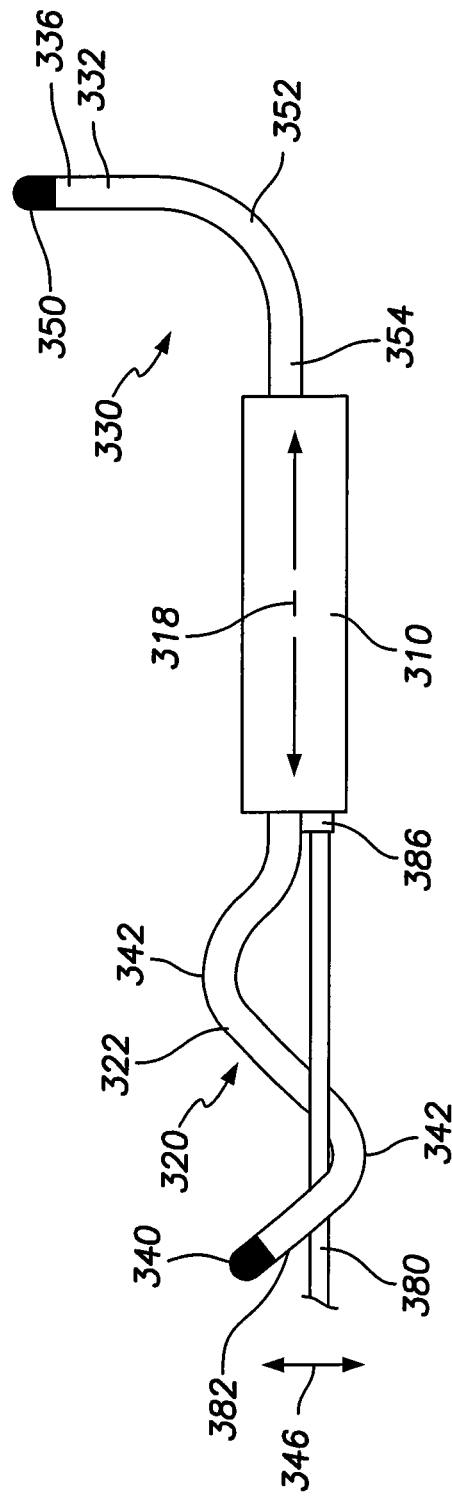
FIG. 3C illustrates the IIMD of FIG. 3A in a fully deployed state at a final deployed stage of the implantation process.

FIG. 3C illustrates the IIMD 310 and both ICDEs 320 and 330 when in fully deployed states at a final deployed stage of the implantation process. As shown in FIG. 3C, the extension body 332 has fully returned to its preformed shape in which the elbow 352 directs the distal leg 356 by a predetermined desired distance into a vessel of interest branching from the coronary sinus. The proximal leg 354 spaces the distal leg 356 a desired distance from the IIMD 310.

Now that the sheath 372 is entirely removed from the ICDE 320, the extension body 322 is permitted to return to its preformed shape. In the example of FIGS. 3A-3C, preformed shape of extension body 322 represents an S or serpentine shape having one or more bends 342 with an electrode 340 located at the distal end 382. The bends 342 caused the ICDE 320 to laterally expand or flare in the transverse direction 346 thereby forcing the electrode 340 to passively but securely abut against and engage the wall of the vessel in which the implant site is designated. Optionally, the extension body 320 may be preformed into a variety of other shapes, such as an L shape, a C shape, a spiral shape, a scissor shape and the like.

The pusher 380 maintains engagement at connector 386 to the IIMD 310 to facilitate final adjustment of the ICDEs 320 and 330 at each stage before, while and after the sheath 372 has been removed. Once the ICDEs 320 and 330 and the IIMD 310 are in final desired positions, the pusher 380 is disconnected at connector 386. The connection at 386 may be formed in a variety of manners as discussed herein.

Figure 4:
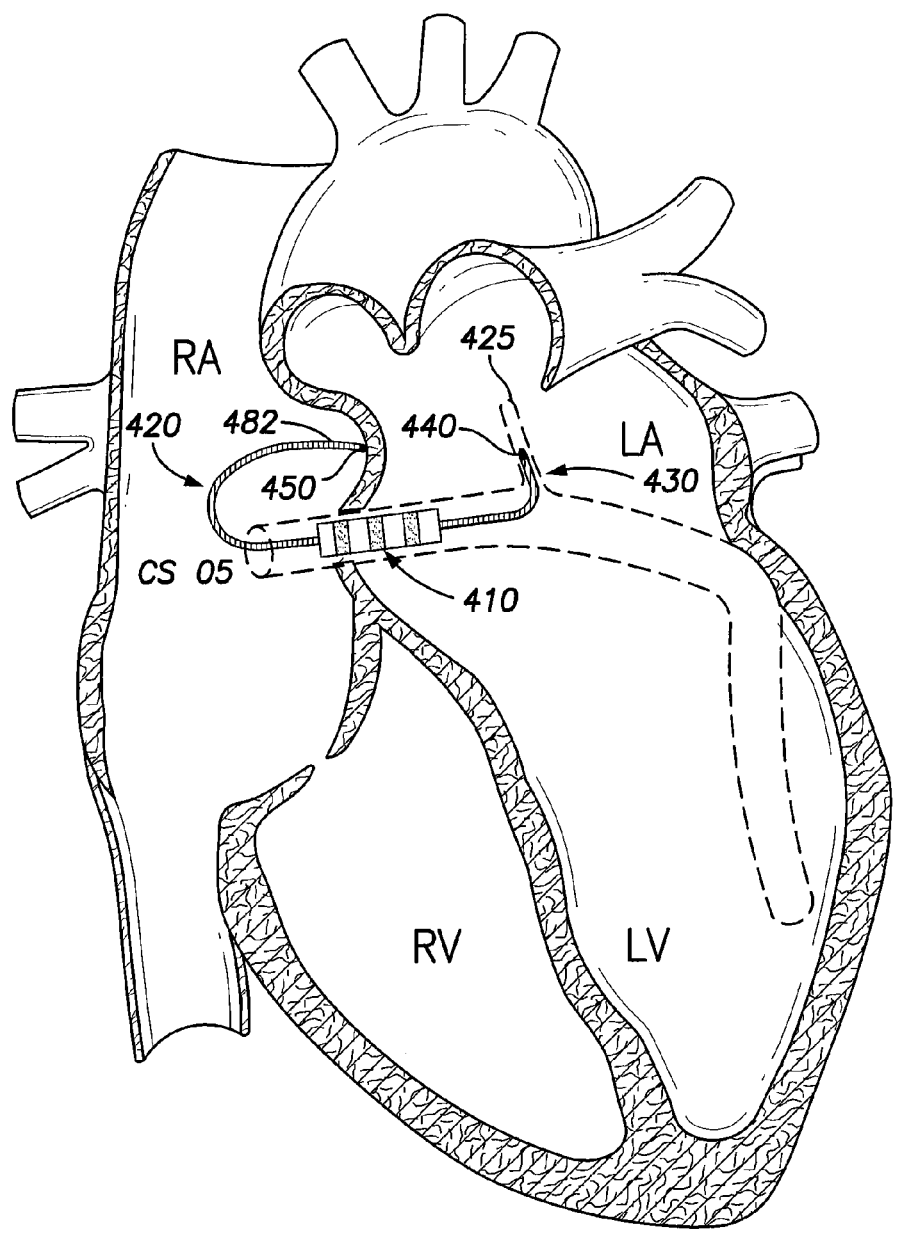
FIG. 4 illustrates a system form in accordance with an alternative embodiment.
Figure 6:
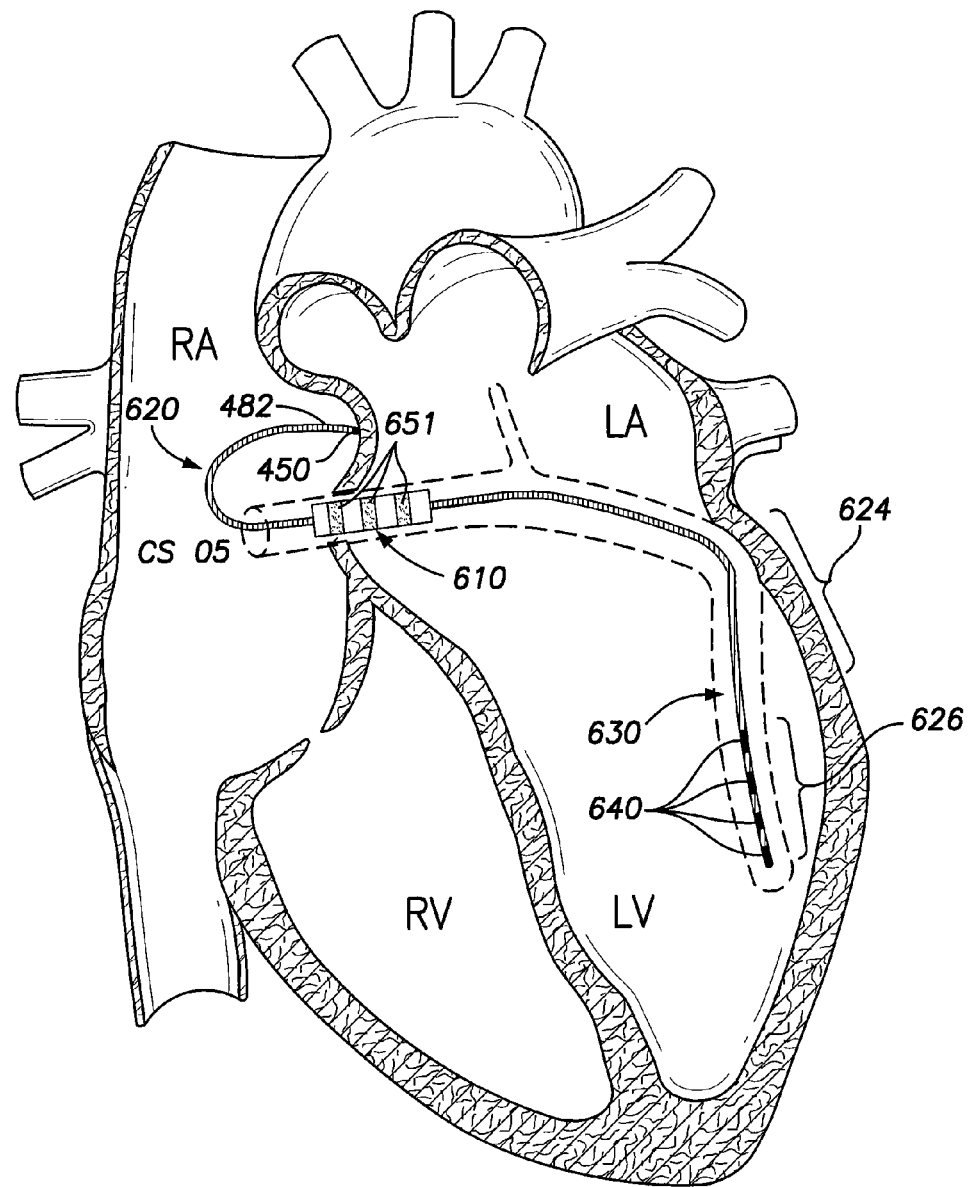
FIG. 6 illustrates a system form in accordance with an alternative embodiment.

FIG. 4 illustrates a system form in accordance with an alternative embodiment. In FIG. 4, the IIMD 410 is located in the coronary sinus, but proximate to the OS. The IIMD 410 has first and second ICDEs 420 and 430 extending from opposite ends thereof. The ICDE 430 is formed longer than those discussed above in connection with other embodiments to be implanted into the lateral or great cardiac vein near the LV. The ICDE 420 has been modified to be longer to extend through the OS back into the RA, such as to the RAA. As shown in FIG. 6, the ICDE 420 has a longer extension body that is preformed into a C or U shape with the distal end 482 wrapping back and abutting against the wall of the RA such that an electrode 450 securely abuts against the wall of the RA at a activation site of interest. As one example, the electrode 450 may extend into the right atrial appendage and abut against an electrically engaged tissue in the RAA. Alternatively, the ICDE 420 may be shaped such that the extension body wraps back until the distal end 482 is located proximate to the atrial septum such that the electrode 450 electrically engages the atrial septum.

Figure 5:
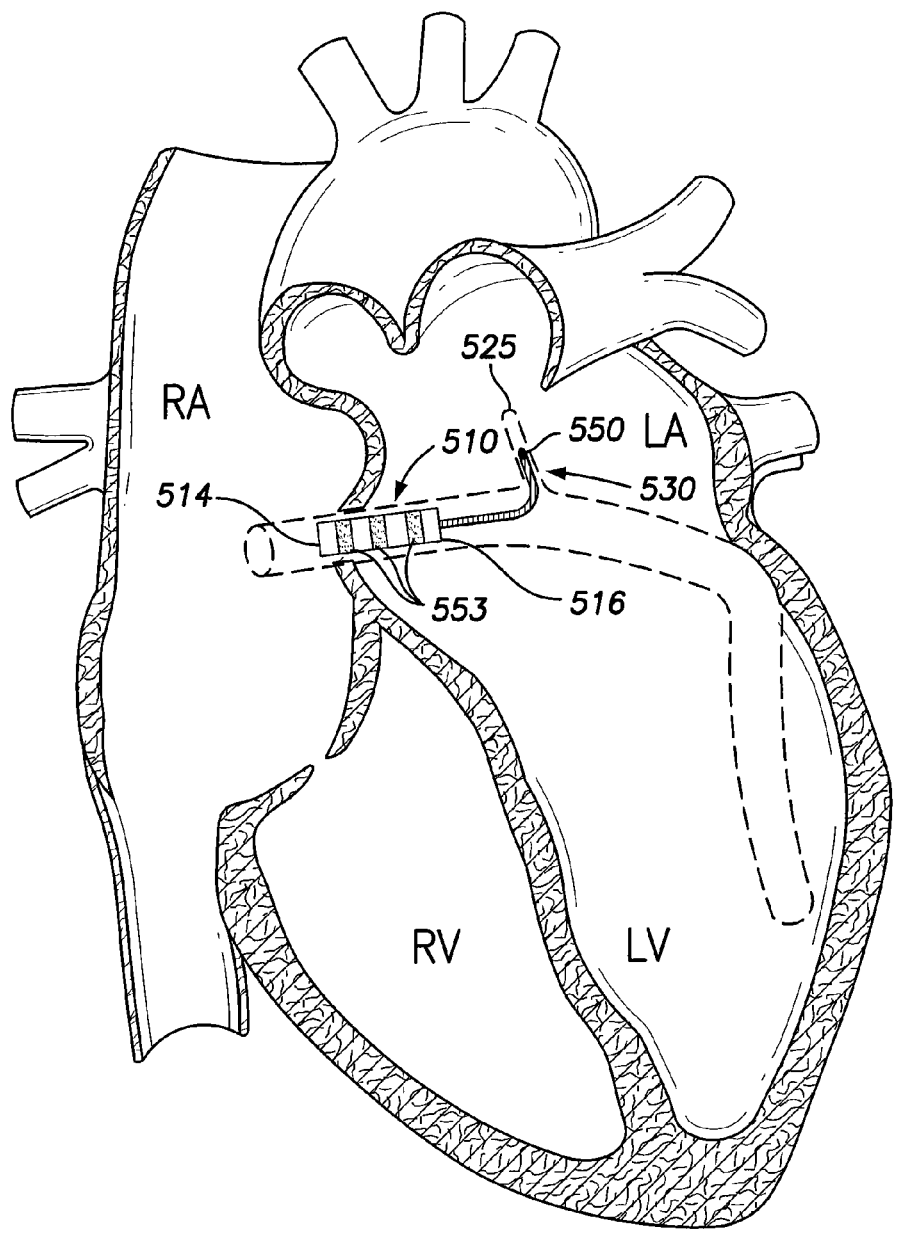
FIG. 5 illustrates a system form in accordance with an alternative embodiment.

FIG. 5 illustrates a system form in accordance with an alternative embodiment. The system includes an IIMD 510 that only has a single ICDE 530 extending from the distal end 516 of the IIMD 510. The ICDE 530 extends along the CS away from the ostium and bends laterally or transversely into the vein of Marshall. The ICDE 530 has an extension body with a length sufficient to locate an electrode 550 distally from the IIMD 510 by a distance sufficient to position the electrode 550 proximate to an activation site proximate to the LA.

The IIMD 510 does not include an ICDE on the proximal end 514. The proximal end 514 is extensionless. Instead, the IIMD 510 has one or more electrodes 553 provided on the housing thereof. The electrodes 553 position to pace and sense at a activation site of interest, such as proximate to the RA.

FIG. 6 illustrates a system form in accordance with an alternative embodiment. In FIG. 6, the IIMD 610 is located in the coronary sinus, but proximate to the OS. The IIMD 610 has first and second ICDEs 620 and 630 extending from opposite ends thereof. The ICDE 630 is formed longer than those discussed above in connection with other embodiments to be implanted into the lateral or great cardiac vein near the LV. The ICDE 620 has been modified to be longer to extend through the OS back into the RA, such as to the RAA. As shown in FIG. 6, the ICDE 620 has a longer extension body that is preformed into a C or U shape with the distal end 682 wrapping back and abutting against the wall of the RA such that an electrode 650 securely abuts against the wall of the RA at a activation site of interest. As one example, the electrode 650 may extend into the right atrial appendage and abut against an electrically engaged tissue in the RAA. Alternatively, the ICDE 620 may be shaped such that the extension body wraps back until the distal end 682 is located proximate to the atrial septum such that the electrode 650 electrically engages the atrial septum.

The ICDE 630 includes an active segment 626 that is joined by a transition segment 624 to the IIMD 610. The active segment 626 includes multiple electrodes 640, such as in a quadripole configuration. The electrodes 640 may be electrically coupled to the sensing and pacing circuits in the IIMD 610 through individual or a common conductors extending along the transition segment 624. The electrodes 640 pace and sense in the LV. The housing of the IIMD 610 includes one or more electrodes 651 positioned to afford LA pacing and sensing.

The ICDEs described herein may be formed with shape memory characteristics that allow the ICDEs to transform between a collapsed state, in which the ICDEs assumes a substantially linear shape, and an expanded state, in which the ICDEs assumes a multi-curved shape. In one embodiment and depending on the vessel designed for implant, the curved configuration of the ICDEs may comprise multiple tightly curved segments, obtusely curved segments, generally linear regions and the like. The number, length, and order of the segments and regions, as well as the degree to which individual segments or regions are curved or linear may vary depending upon the anatomical contour to be followed. The shaped ICDEs are formed into a pre-loaded shape in which various regions or segments extend along desired arcuate paths and project from longitudinal/lateral axes at desired pitch, roll and yaw angles, where the pitch, roll and yaw angles are measured from reference angular positions.

The IIMD may be operated in various modes, such as in select pacemaker modes, select cardiac resynchronization therapy modes, a cardioversion mode, a defibrillation mode and the like. For example, a typical pacing mode may include DDD, VVV, DDIR, DDDR and the like, where the first letter indicates the chamber(s) paced (e.g., A: Atrial pacing; V: Ventricular pacing; and D: Dual-chamber (atrial and ventricular) pacing). The second letter indicates the chamber in which electrical activity is sensed (e.g., A, V, or D). The code O is used when pacemaker discharge is not dependent on sensing electrical activity. The third letter refers to the response to a sensed electric signal (e.g., T: Triggering of pacing function; I: Inhibition of pacing function; D: Dual response (i.e., any spontaneous atrial and ventricular activity will inhibit atrial and ventricular pacing and lone atrial activity will trigger a paced ventricular response) and O: No response to an underlying electric signal (usually related to the absence of associated sensing function)). The fourth letter indicates rate responsive if R is present. As one example, the IIMD may be configured with DDI, DDO, DDD or DDDR mode-capability when placed at a local activation site in the RA.

Figure 7:
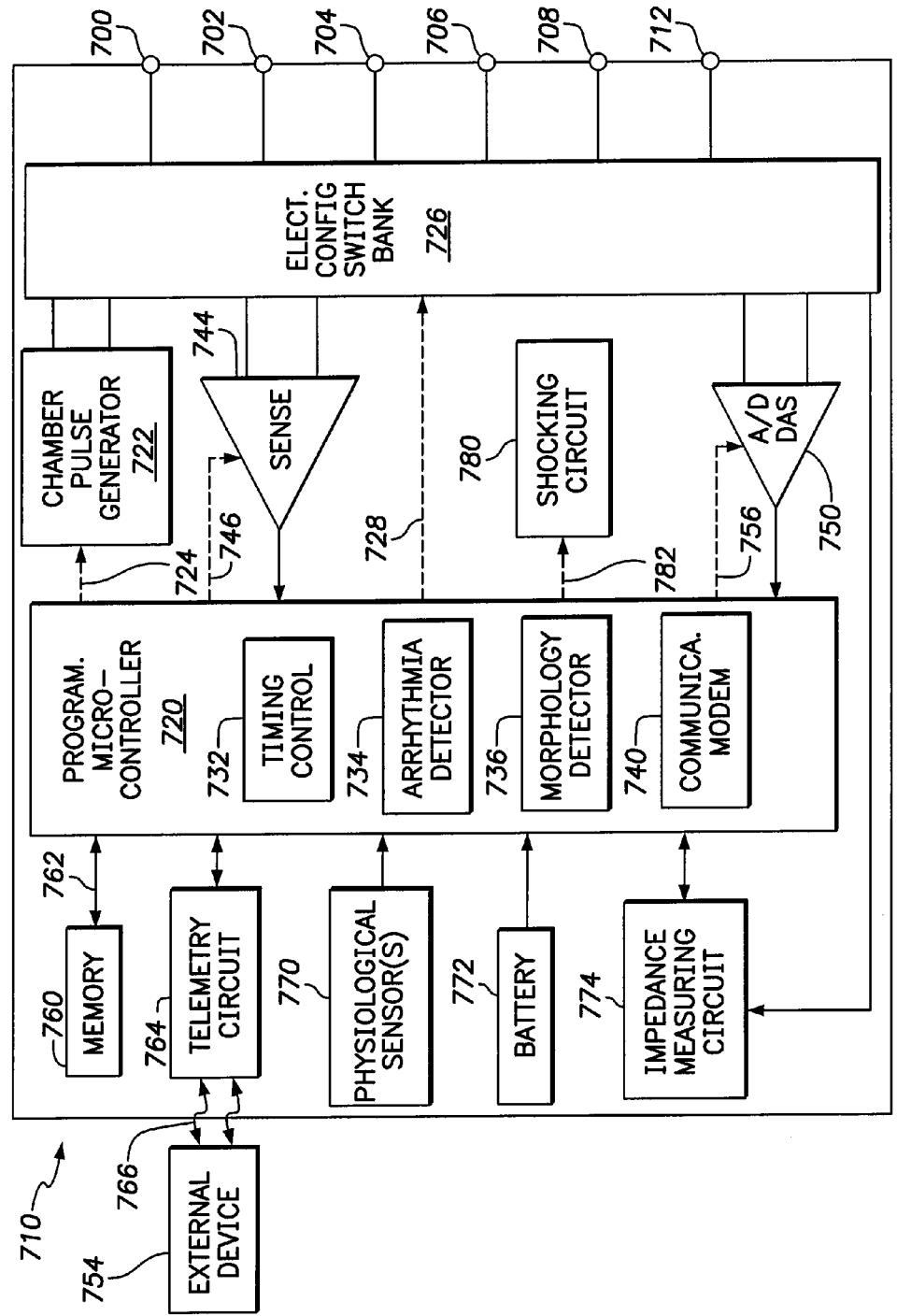
FIG. 7 shows a block diagram of an IIMD, implemented in accordance with an embodiment.

FIG. 7 shows a block diagram of an IIMD 710, which may be implemented as IIMDs 10, 310, 410, 510 and 610, that are implanted in accordance with embodiments. The IIMD 710 may be implemented as a full-function biventricular pacemaker, equipped with both atrial and ventricular sensing and pacing circuitry for four chamber sensing and stimulation therapy (including both pacing and shock treatment). Optionally, the IIMD 710 may provide full-function cardiac resynchronization therapy. Alternatively, the IIMD 710 may be implemented with a reduced set of functions and components. For instance, the IIMD 710 may be implemented without ventricular sensing and pacing.

The IIMD 710 has a housing 700 to hold the electronic/computing components. The housing 700 (which is often referred to as the "can", "case", "encasing", or "case electrode") may be programmably selected to act as the return electrode for certain stimulus modes. Housing 700 further includes a connector (not shown) with a plurality of terminals 702, 704, 706, 708, and 712. The terminals may be connected to electrodes that are located in various locations within and about the heart. For example, the terminals may include: a terminal 702 to be coupled to a first electrode or first set of electrodes (e.g. electrodes 40, 340, and 440) located in or near a first activation site; a terminal 704 to be coupled to a second electrode or second set of electrodes (e.g. 50, 350, 450, and 550) located in or near a second activation site; a terminal 706 to be coupled to a third electrode or third set of electrodes located in or near the first or second activation site; terminals 708 and 710 to be coupled to a fourth electrode or fourth set of electrodes located in or near the a third activation site. The type and location of each electrode may vary. For example, the electrodes may include various combinations of ring, tip, coil and shocking electrodes and the like.

The IIMD 710 includes a programmable microcontroller 1020 that controls various operations of the IIMD 710, including cardiac monitoring and stimulation therapy. Microcontroller 720 includes a microprocessor (or equivalent control circuitry), RAM and/or ROM memory, logic and timing circuitry, state machine circuitry, and I/O circuitry.

IMD 710 further includes a first chamber pulse generator 722 that generates stimulation pulses for delivery by one or more electrodes coupled thereto. The pulse generator 722 is controlled by the microcontroller 720 via control signal 724. The pulse generator 722 is coupled to the select electrode(s) via an electrode configuration switch 726, which includes multiple switches for connecting the desired electrodes to the appropriate I/O circuits, thereby facilitating electrode programmability. The switch 726 is controlled by a control signal 628 from the microcontroller 720.

In the example of FIG. 7, a single pulse generator 722 is illustrated. Optionally, the IIMD 710 may include multiple pulse generators, similar to pulse generator 722, where each pulse generator is coupled to one or more electrodes and controlled by the microcontroller 720 to deliver select stimulus pulse(s) to the corresponding one or more electrodes.

Microcontroller 720 is illustrated as including timing control circuitry 732 to control the timing of the stimulation pulses (e.g., pacing rate, atrio-ventricular (AV) delay, atrial interconduction (A-A) delay, or ventricular interconduction (V-V) delay, etc.). The timing control circuitry 732 may also be used for the timing of refractory periods, blanking intervals, noise detection windows, evoked response windows, alert intervals, marker channel timing, and so on. Microcontroller 720 also has an arrhythmia detector 734 for detecting arrhythmia conditions and a morphology detector 736. Although not shown, the microcontroller 720 may further include other dedicated circuitry and/or firmware/software components that assist in monitoring various conditions of the patient's heart and managing pacing therapies.

The IIMD 710 is further equipped with a communication modem (modulator/demodulator) 740 to enable wireless communication with the remote slave pacing unit 706. In one implementation, the communication modem 740 uses high frequency modulation. As one example, the modem 740 transmits signals between a pair of electrodes of the lead assembly 704, such as between the can 700 and the right ventricular tip electrode 722. The signals are transmitted in a high frequency range of approximately 20-80 kHz, as such signals travel through the body tissue in fluids without stimulating the heart or being felt by the patient.

The communication modem 740 may be implemented in hardware as part of the microcontroller 720, or as software/firmware instructions programmed into and executed by the microcontroller 720. Alternatively, the modem 740 may reside separately from the microcontroller as a standalone component.

The IIMD 710 includes sensing circuitry 744 selectively coupled to one or more electrodes that perform sensing operations, through the switch 726 to detect the presence of cardiac activity in the corresponding chambers of the heart. The sensing circuit 744 is configured to perform bipolar sensing between one pair of electrodes and/or between multiple pairs of electrodes. The sensing circuit 744 detects NF electrical activity and rejects FF electrical activity. The sensing circuitry 744 may include dedicated sense amplifiers, multiplexed amplifiers, or shared amplifiers. It may further employ one or more low power, precision amplifiers with programmable gain and/or automatic gain control, bandpass filtering, and threshold detection circuit to selectively sense the cardiac signal of interest. The automatic gain control enables the unit to sense low amplitude signal characteristics of atrial fibrillation. Switch 726 determines the sensing polarity of the cardiac signal by selectively closing the appropriate switches. In this way, the clinician may program the sensing polarity independent of the stimulation polarity.

The output of the sensing circuitry 744 is connected to the microcontroller 720 which, in turn, triggers or inhibits the pulse generator 722 in response to the absence or presence of cardiac activity. The sensing circuitry 744 receives a control signal 746 from the microcontroller 720 for purposes of controlling the gain, threshold, polarization charge removal circuitry (not shown), and the timing of any blocking circuitry (not shown) coupled to the inputs of the sensing circuitry.

In the example of FIG. 7, a single sensing circuit 744 is illustrated. Optionally, the IIMD 710 may include multiple sensing circuit, similar to sensing circuit 744, where each sensing circuit is coupled to one or more electrodes and controlled by the microcontroller 720 to sense electrical activity detected at the corresponding one or more electrodes. The sensing circuit 744 may operate in a unipolar sensing configuration or in a bipolar sensing configuration.

The IIMD 710 further includes an analog-to-digital (A/D) data acquisition system (DAS) 750 coupled to one or more electrodes via the switch 726 to sample cardiac signals across any pair of desired electrodes. The data acquisition system 750 is configured to acquire intracardiac electrogram signals, convert the raw analog data into digital data, and store the digital data for later processing and/or telemetric transmission to an external device 754 (e.g., a programmer, local transceiver, or a diagnostic system analyzer). The data acquisition system 750 is controlled by a control signal 756 from the microcontroller 720.

The microcontroller 720 is coupled to a memory 760 by a suitable data/address bus 762. The programmable operating parameters used by the microcontroller 720 are stored in memory 760 and used to customize the operation of the IIMD 710 to suit the needs of a particular patient. Such operating parameters define, for example, pacing pulse amplitude, pulse duration, electrode polarity, rate, sensitivity, automatic features, arrhythmia detection criteria, and the amplitude, wave shape and vector of each shocking pulse to be delivered to the patient's heart 708 within each respective tier of therapy.

The operating parameters of the IIMD 710 may be non-invasively programmed into the memory 760 through a telemetry circuit 764 in telemetric communication via communication link 766 with the external device 754. The telemetry circuit 764 allows intra-cardiac electrograms and status information relating to the operation of the IIMD 710 (as contained in the microcontroller 720 or memory 760) to be sent to the external device 754 through the established communication link 766.

The IIMD 710 can further include magnet detection circuitry (not shown), coupled to the microcontroller 720, to detect when a magnet is placed over the unit. A magnet may be used by a clinician to perform various test functions of the unit 710 and/or to signal the microcontroller 720 that the external programmer 754 is in place to receive or transmit data to the microcontroller 720 through the telemetry circuits 764.

The IIMD 710 can further include one or more physiologic sensors 770. Such sensors are commonly referred to as "rate-responsive" sensors because they are typically used to adjust pacing stimulation rates according to the exercise state of the patient. However, the physiological sensor 770 may further be used to detect changes in cardiac output, changes in the physiological condition of the heart, or diurnal changes in activity (e.g., detecting sleep and wake states). Signals generated by the physiological sensors 770 are passed to the microcontroller 720 for analysis. The microcontroller 720 responds by adjusting the various pacing parameters (such as rate, AV Delay, V-V Delay, etc.) at which the atrial and ventricular pacing pulses are administered. While shown as being included within the unit 710, the physiologic sensor(s) 770 may be external to the unit 710, yet still be implanted within or carried by the patient. Examples of physiologic sensors might include sensors that, for example, sense respiration rate, pH of blood, ventricular gradient, activity, position/posture, minute ventilation (MV), and so forth.

A battery 772 provides operating power to all of the components in the IIMD 710. The battery 772 is capable of operating at low current drains for long periods of time, and is capable of providing high-current pulses (for capacitor charging) when the patient requires a shock pulse (e.g., in excess of 2 A, at voltages above 2 V, for periods of 10 seconds or more). The battery 772 also desirably has a predictable discharge characteristic so that elective replacement time can be detected. As one example, the unit 710 employs lithium/silver vanadium oxide batteries.

The IIMD 710 further includes an impedance measuring circuit 774, which can be used for many things, including: lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves; and so forth. The impedance measuring circuit 774 is coupled to the switch 726 so that any desired electrode may be used. The microcontroller 720 further controls a shocking circuit 780 by way of a control signal 782. The shocking circuit 780 generates shocking pulses of low (e.g., up to 0.5 joules), moderate (e.g., 0.5-10 joules), or high energy (e.g., 10 to 40 joules), as controlled by the microcontroller 720.

Optionally, in an alternative embodiment, an entirely separate IIMD device may be provided with an active fixation helix or other fixation mechanism to secure the second IIMD directly into a chamber of interest, such as the right atrium in order to afford bi-atrial pacing in an alternative configuration.

Optionally, in an alternative configuration, the second IIMD with an active fixation mechanism may be provided in the atrial septum in order to provide pacing pulses into the atrial septum and thereby capture both right atrium and left atrium through the same pacing stimulus as an alternative manner of managing AF.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and coatings described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. §72, sixth paragraph, unless and until such claim limitations expressly use the phrase "means for" followed by a statement of function void of further structure.

What is claimed is:

1. An intra-cardiac implantable medical device (IIMD), comprising:
    a housing configured to be implanted entirely within a coronary sinus (CS) of the heart, the housing including opposed proximal and distal ends, the housing configured to be positioned at a first implant location within the CS such that the proximal end is directed toward an ostium (OS) and the distal end is directed toward vessels branching from the CS;
    a first intra-cardiac device extension (ICDE) having a first extension body that is electrically and physically attached to the proximal end of the housing, the first extension body including a first transition segment and a first active segment, the first transition segment adapted to extend along the CS toward the OS;
    a first electrode provided on the first active segment and configured to be positioned at a first activation site proximate to a first chamber of interest when the first extension body is in a fully deployed state;
    a second ICDE having a second extension body that is electrically and physically attached to the distal end of the housing, the second extension body including a second transition segment and a second active segment, the second transition segment adapted to extend along the CS away from the OS toward a vessel of interest;
    a second electrode provided on the second active segment and configured to be positioned at a second activation site proximate to a second chamber of interest when the second extension body is in a fully deployed state; and
    a controller, within the housing, configured to cause stimulus pulses to be delivered, in synchronous manner, through the first and second electrodes to the first and second activation sites, respectively.

2. The IIMD of claim 1, wherein the first and second transition segments are sufficient in length to locate the first and second active segments distal from the housing of the IIMD such that the first and second electrodes are located in at least one of a right atrium, the CS, a tributary vein near the LV and a vein of Marshall branching from the CS.

3. The IIMD of claim 1, wherein the first transition segment is sufficient in length to extend back through the OS to locate the first active segment distal from the housing of the IIMD with the first electrode located at the first activation site in a right atrium.

4. The IIMD of claim 1, wherein the second transition segment is sufficient in length to extend into the vein of Marshall to locate the second active segment distal from the housing of the IIMD with the second electrode located in the vein of Marshall and proximate to the second activation site in a left atrium.

5. The IIMD of claim 1, further comprising a third electrode provided on the housing, the third electrode configured to be located proximate to a third implant side, the third implant side associated with one of the right atrium and left atrium.

6. The IIMD of claim 1, wherein the first extension body is formed of a flexible biocompatible material having a preformed curved shape with at least first and second bends that project in opposed transverse directions, relative to a longitudinal axis of the housing, to engage the vessel of interest when in the deployed state.

7. The IIMD of claim 1, wherein the second extension body is formed of a flexible biocompatible material having a preformed L-shape with an elbow portion provided between proximal and distal leg portions, the elbow directing the distal leg into the vein of Marshall.

8. The IIMD of claim 1, wherein the first and second extension bodies are formed of materials having shape memory characteristics that allow the first and second extension bodies to transform between a collapsed state and an expanded deployed state.

9. The IIMD of claim 1, wherein the controller is configured to identify atrial fibrillation and cause delivery of an atrial antitachycardia pacing (AATP) therapy.

* * * * *